(12) United States Patent
Lee (10) Patent No.: US 7,489,399 B1
(45) Date of Patent: Feb. 10, 2009

(54) SPECTROSCOPIC MULTI ANGLE ELLIPSOMETRY

(75) Inventor: Shing Lee, Fremont, CA (US)

(73) Assignee: KLA-Tencor Corporation, San Jose, CA (US)

( * ) Notice: Subject to any disclaimer, the term of this patent is extended or adjusted under 35 U.S.C. 154(b) by 522 days.

(21) Appl. No.: 10/923,325

(22) Filed: Aug. 20, 2004

(51) Int. Cl.
*G01J 4/00* (2006.01)
(52) U.S. Cl. .................................... 356/369
(58) Field of Classification Search ......... 356/364–369; 359/246, 247, 251, 283, 371, 437, 501
See application file for complete search history.

(56) References Cited

U.S. PATENT DOCUMENTS

| | | | |
|---|---|---|---|
| 3,158,675 A * | 11/1964 | Hanyo et al. ............... | 356/367 |
| 3,482,182 A * | 12/1969 | Kosanke et al. ............. | 372/24 |
| 4,999,014 A | 3/1991 | Gold et al. ................. | 356/632 |
| 5,042,591 A | 8/1991 | Hull .......................... | 173/91 |
| 5,166,752 A | 11/1992 | Spanier et al. ............. | 356/369 |
| 5,432,607 A * | 7/1995 | Taubenblatt ................ | 356/364 |
| 5,504,582 A * | 4/1996 | Johs et al. .................. | 356/369 |
| 5,521,706 A * | 5/1996 | Green et al. ................ | 356/369 |
| 5,872,630 A * | 2/1999 | Johs et al. .................. | 356/369 |
| 6,052,188 A * | 4/2000 | Fluckiger et al. ........... | 356/369 |
| 6,256,097 B1 | 7/2001 | Wagner ...................... | 356/369 |
| 6,275,291 B1 * | 8/2001 | Abraham et al. ........... | 356/367 |
| 6,483,584 B1 * | 11/2002 | Lee et al. .................... | 356/369 |
| 6,714,300 B1 * | 3/2004 | Rosencwaig et al. ....... | 356/369 |
| 6,822,738 B1 * | 11/2004 | Johs et al. .................. | 356/369 |
| 6,934,025 B2 * | 8/2005 | Opsal et al. ................ | 356/369 |
| 7,061,601 B2 * | 6/2006 | Meeks ........................ | 356/237.2 |
| 2002/0008874 A1 * | 1/2002 | Lee et al. .................... | 356/369 |

* cited by examiner

*Primary Examiner*—Hwa (Andrew) S Lee
*Assistant Examiner*—Jonathon D Cook
(74) *Attorney, Agent, or Firm*—Luedeka, Neely & Graham, P.C.

(57) ABSTRACT

An ellipsometer having a light source for generating a probe beam along a probe beam path. A polarizing beam splitter passes the probe beam along the probe beam path, at least in part, as the probe beam passes through the beam splitter in a first direction, and diverts the probe beam along a detection path, at least in part, as the probe beam passes through the beam splitter in a second direction that is substantially opposite of the first direction. A compensator variably retards at least portions of the probe beam along at least one axis of the compensator, thereby changing an orientation of the light passing through the compensator. Optics focus the probe beam on a spot on a substrate. A concave mirror receives the probe beam from the spot on the substrate as it travels along the probe beam path in the first direction, and sends the probe beam back along the probe beam path in the second direction. A detector receives the probe beam along the detection path. Preferably, all of the elements of the ellipsometer that are disposed along the probe beam path are fixed and do not rotate relative to the probe beam during measurement operations.

18 Claims, 5 Drawing Sheets

SPECTROSCOPIC MULTI ANGLE ELLIPSOMETRY

FIELD

This invention relates to the field of integrated circuit fabrication. More particularly, this invention relates to ellipsometry for measuring film thicknesses on integrated circuits.

BACKGROUND

As the integrated circuit fabrication industry continually moves to improve yield, there is a need to provide faster feedback so as to catch any drifts in the process as early as possible. Thus, there has been much activity in the field of integrated circuit metrology. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

Ellipsometry has been used extensively in integrated circuit metrology. To meet the desired precision for complicated film stacks, ellipsometry has generally been implemented with either multi wavelength or multi angle approaches. A wide wavelength range is generally desirable for spectroscopic ellipsometry. However, chromatic aberrations tend to create serious challenges when attempting to focus the beam to a small spot on the substrate, and then process all of the wavelengths in the desired range at the same time. Thus, these two approaches are typically enabled with the use of one or more rotating elements within the ellipsometer. Therefore, ellipsometers having rotating elements are one current method of implementing a multi wavelength solution.

High performance rotation-based spectroscopic ellipsometers employed in integrated circuit fabrication units tend to fall into one of two generally classes of instruments. The first class is generally referred to as a rotating polarizer, and the second class is generally referred to as a rotating analyzer or compensator. Because of the difficulty involved in integrating these two types of ellipsometers into process modules that are used for inline integrated circuit inspections, a reflectometer is generally used for such measurements, instead of an ellipsometer.

The use of a motor in the ellipsometer, to provide the rotation capability, has been one of the biggest reliability problems, and adds greatly to the cost of the ellipsometer. The motor should be controlled very accurately in order to produce accurate and repeatable measurements. Therefore, large encoders have been used with the motors to ensure accurate placement of the rotating elements, and the rotation of the elements is typically limited to a speed that is on the order of a few Hertz. In addition, lamp noise and mechanical stability have been a major source of system error in ellipsometers. Therefore, these systems tend to be stand alone units, where the reliability requirement is less stringent than in an inline process module.

Another method to implement a multi wavelength solution is to use a focusing element based on all reflective optics to obtain the ellipsometric parameters. Based on such reflective optics, an ultra-wide spectrum of light, from vacuum ultra violet to infrared, can be collimated and focused onto a very small spot for spectroscopic ellipsometric measurements.

Figure 11:
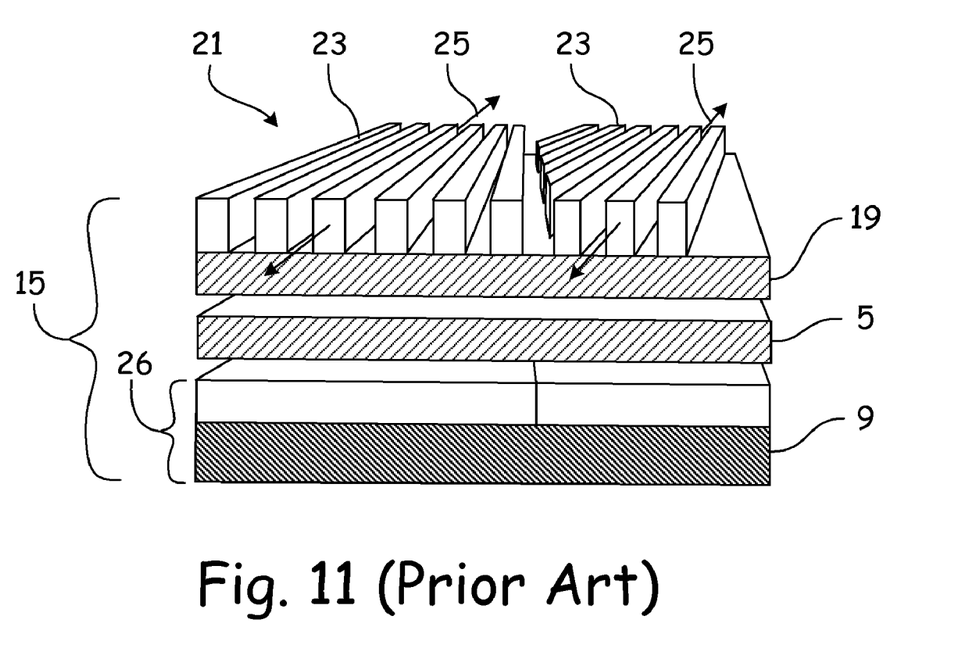
FIG. 11 is a prior art diagram of a grooved wave plate on a detector.

Yet another approach is disclosed in U.S. Pat. No. 6,275,291, the disclosure of which is included by reference herein as if laid out in its entirety, and uses sub wavelength-spaced grooves that are aligned along different orientations. As disclosed in the latter-referenced patent above, FIG. 11 depicts a wave plate 21 mounted onto a detector 26, to form a combined structure 15. Two pixels 23 of the wave plate 21 are shown. The pixels 23 are formed by two grids, the major axis orientations 25 of which are at different angles. The grid structures 23 are preferably made of a transparent material, and form a unit with the transparent retarder substrate 19. Typical dimensions of such grid structures 23 are: width 200 millimeters, trench width 200 microns, depth 400 microns. When the light 12 falls on these structures, the surface reacts like an artificially generated anisotropic material, similar to the anisotropic crystals used in conventional optics for the manufacture of retarders.

These grids of the pixels 23 can be manufactured by means of electron beam lithography in combination with ion beam etching processes. After the manufacture of the grid, the grid substrate unit is preferably attached, such as by an adhesive, to the analyzer 5, and the latter is in turn connected to the detector 26, which preferably has a substrate 9 on which the charge coupled device pixels are located. The position of the axis of the analyzer 5 is preferably selected so that it does not coincide with one of the major axes 25 of the retarder 23. This becomes possible if the angles of the major axes 25 within a pixel group vary by about thirty degrees, while the axis of the analyzer 5 is at about forty-five degrees. The groove pitch of the pixels 23 is preferably less than the wavelength of the light 12. The orientation of the light 12 coming off of the grooves in the pixels 23 tends to change across the surface of the detector 26, acting like a rotating compensator. Therefore, no moving parts are needed for this approach.

However, there are a number of process related issues with this approach as describe in the latter-referenced patent. For example, the pixel 23 on the micro wave plate 15 and the charge coupled device 26 must line up. Further, electron beam and ion etch processes are needed to fabricate the wave plate. Variations in these processes tend to give inconsistent retardation and orientation across the charge coupled device, and the lithography processes used are not good at writing slanted lines at arbitrary orientation. The variations in the micro wave plate create problems with system-to-system matching. In addition, a large number of unknowns need to be calibrated. The unknowns determined through calibration tend to make it an inaccurate measurement system.

As introduced above, although reflectometers are typically used for integrated critical dimension and film metrology for the reasons given above, it is well known that ellipsometry is much more sensitive than reflectometry, since ellipsometry measures the change in polarization states, and is much less sensitive to lamp noise and transmission loss over time.

What is needed, therefore, is an ellipsometer that reduces, at least in part, some of the problems described above.

SUMMARY

The above and other needs are met by an improvement to an ellipsometer having a fixed, non rotating compensator for receiving a probe beam of light along a probe beam path. The compensator is adapted to variably retard at least portions of the probe beam along at least one axis of the compensator, thereby changing an orientation of the light passing through the compensator.

Thus, the present invention provides a new concept of ellipsometry without moving parts, which uses a compensator with known birefringence along one direction. The ellipsometer disclosed herein has no parts that need to be moved during measurement operations, and therefore is faster, less sensitive to lamp noise, more reliable, and has a smaller form factor. The ellipsometer disclosed herein is especially suitable for inline integrated circuit metrology.

In various embodiments, the compensator is Babinet compensator. Preferably, no elements of the ellipsometer that are disposed along the probe beam path rotate during measurement, and most preferably all the elements are fixed. The ellipsometer preferably includes a polarizing beam splitter, and a concave mirror which sends a probe beam back through the probe beam path, which replace collection optics, a polarizer, and an analyzer of the ellipsometer. Most preferably, the concave mirror is partially reflective, and at least one of a focus sensor, a tilt sensor, and combination focus and tilt sensor are disposed behind the concave mirror, which enables calibration of the ellipsometer on the probe beam.

The ellipsometer is preferably a spectroscopic ellipsometer having a cylindrical mirror for separating wavelengths of the probe beam as it enters a detector. In some embodiments the ellipsometer measures ellipsometric parameters in both angle and wavelength with a Fourier transform spectrometer. Image resolution noise is preferably reduced by separating a spatial spectrum content of the probe beam with a prism. A dispersive element preferably displaces the probe beam according to wavelength components of the probe beam, with shorter wavelengths of the probe beam striking a top of a focusing element, and longer wavelengths of the probe beam striking a bottom of the focusing element, thereby providing the ellipsometer with a wavelength dependent angle of incidence.

According to another aspect of the invention there is described an ellipsometer having a light source for generating a probe beam along a probe beam path. A polarizing beam splitter passes the probe beam along the probe beam path, at least in part, as the probe beam passes through the beam splitter in a first direction, and diverts the probe beam along a detection path, at least in part, as the probe beam passes through the beam splitter in a second direction that is substantially opposite of the first direction. A compensator variably retards at least portions of the probe beam along at least one axis of the compensator, thereby changing an orientation of the light passing through the compensator. Optics focus the probe beam on a spot on a substrate. A concave mirror receives the probe beam from the spot on the substrate as it travels along the probe beam path in the first direction, and sends the probe beam back along the probe beam path in the second direction. A detector receives the probe beam along the detection path. Preferably, all of the elements of the ellipsometer that are disposed along the probe beam path are fixed and do not rotate relative to the probe beam during measurement operations.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

This various embodiments of the present invention described herein generally relate to a new type of ellipsometer without moving parts along a probe beam path. Such a system is more compact, more reliable, has higher throughput, and is especially suitable for inline integrated circuit metrology.

Figure 1:
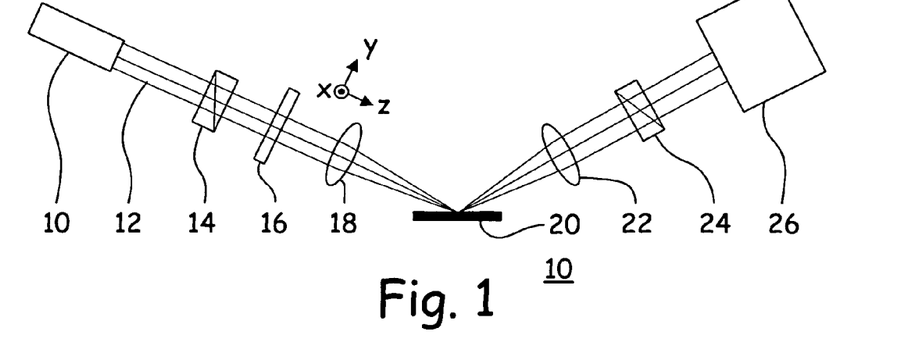
FIG. 1 is a functional diagram of an ellipsometer.
Figure 2:
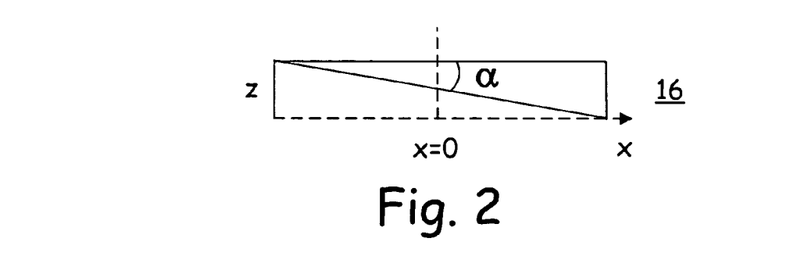
FIG. 2 is a cross sectional representation of a Babinet compensator.
Figure 3:
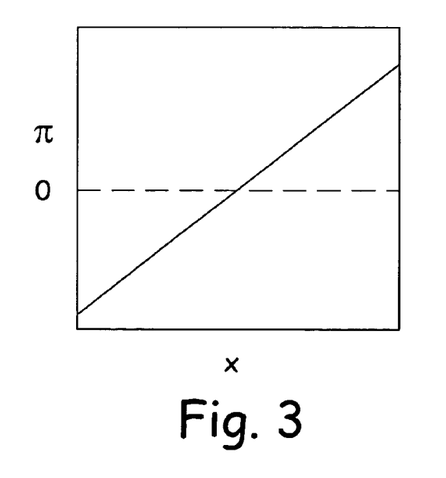
FIG. 3 is a chart of the transmission properties of a compensator.
Figure 4:
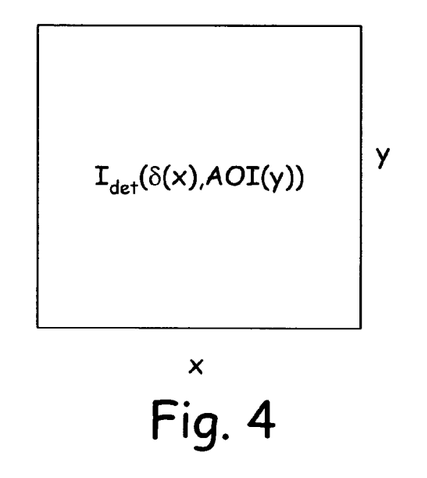
FIG. 4 is a chart of the received light signal at different retardations from the angle of incidence.

The basic embodiment of an ellipsometer 10 according to the present invention is illustrated in FIG. 1. A collimated light 12 is generated by a light source, such as a laser or lamp 10, and passes through a fixed polarizer 14 and a Babinet compensator 16, with the phase varying axis of the compensator 16 along the x-axis, as depicted in FIG. 2. The constant wave front of the collimated light 12 preferably experiences a linear variation of phase retardation between the s-wave and the p-wave as it passes through the compensator 16, as depicted in FIG. 3. As depicted in FIG. 4, the retardation is generally uniform along the y axis, which can be considered as a slow or no retardation axis, and there is preferably a gradual—and most preferably linear—change in retardation along the x axis, which can be considered as a fast retardation axis. The detector preferably senses an image of the retardation, which leaves the x-dependence substantially on the retardence of the compensation, as described more completely below. The y-dependence is preferably a function of the angle of incidence (or AOI as depicted in the equation for FIG. 4). Therefore, ellipsometers according to the present invention can perform ellipsometric measurements on different angles of incidence simultaneously.

Such a retardation profile is preferably selected based at least in part on the relative ease of manufacturing and calibrating such a device. One method of implementing the retardation is with the use of a wave plate 21, such as is described above in regard to FIG. 11 It is appreciated that the present invention is not limited to this specific retardation profile or the use of a wave plate 21 to implement it, but encompasses other retardation profiles and methods of implementation.

As the light 12 focuses down through the optics 18 to the surface of the substrate 20, and is re-collimated by the collection optics 22, it passes the analyzer 24 and impinges onto a detector, such as a charge coupled device array 26. The signal at the detector 26, which is preferably oriented in the xy plane, can be interpreted as a linear variation of the angle of incidence of the light 12 in the y axis and relative s-phase and p-phase retardation along the x-axis. A polarization analysis for such a system for any one row along the x-direction yields:

$$I_{det} = I_0(1 + \tan^2 \psi + 2 \tan \psi \cos(\delta + \Delta))$$

$$\delta = \tan \alpha (n_e - n_o) x$$

The ellipsometric parameters $\tan \Psi$ and $\Delta$ in the equations above can be obtained from the second and third term, such as in the rotating polarizer 14 or compensator 16 approaches. Taking into account the angle of incidence variation in the y-direction, a complete map of ellipsometric parameters as functions of angle of incidence are available for the sample. Therefore, the film stack thicknesses, refractive indices, and extinction coefficients can all be obtained.

The simple relations between film characteristics, wavelength, angle of incidence, retardation orientation of the compensator 16, detector 26 orientation, and the known dispersion of the retardation element, such as a wave plate 21, on the compensator 16, provide a desirable redundancy that can be used for calibration of the ellipsometer 10, and generally increases the accuracy of the ellipsometer 10, which is desirable for use in demanding metrology applications, such as inline measurement. This is in stark contrast to the approach that places a micro wave plate 21 on the detector 26, which is very process and alignment dependent, and for which a large number of factors need to be determined, which render it a relatively inaccurate method. Further, matching one ellipsometry system to another, which very critical for inline metrology, tends to suffer from the process dependent manufacturing process.

The preferred embodiments of the current invention avoid these drawbacks by using a Babinet compensator 16 that has a retardation profile that changes across the surface of the compensator 16. Such a compensator 16 is relatively simple to make with conventional cutting, polishing, and optical contacting. The cut angle, refractive indices for ordinary and extraordinary light rays 12 for all wavelengths used and centered position of the wave plate 21 can all be can be determined relatively easily. A Babinet compensator 16 according to the present invention is thus preferably made with proven conventional technologies. This results in reproducible wave plates with no unknown parameters, and greatly improves the matching and accuracy of the resultant measurement system, as compared to the approach of attaching a micro wave plate 21 to the detector 26.

Figure 5:
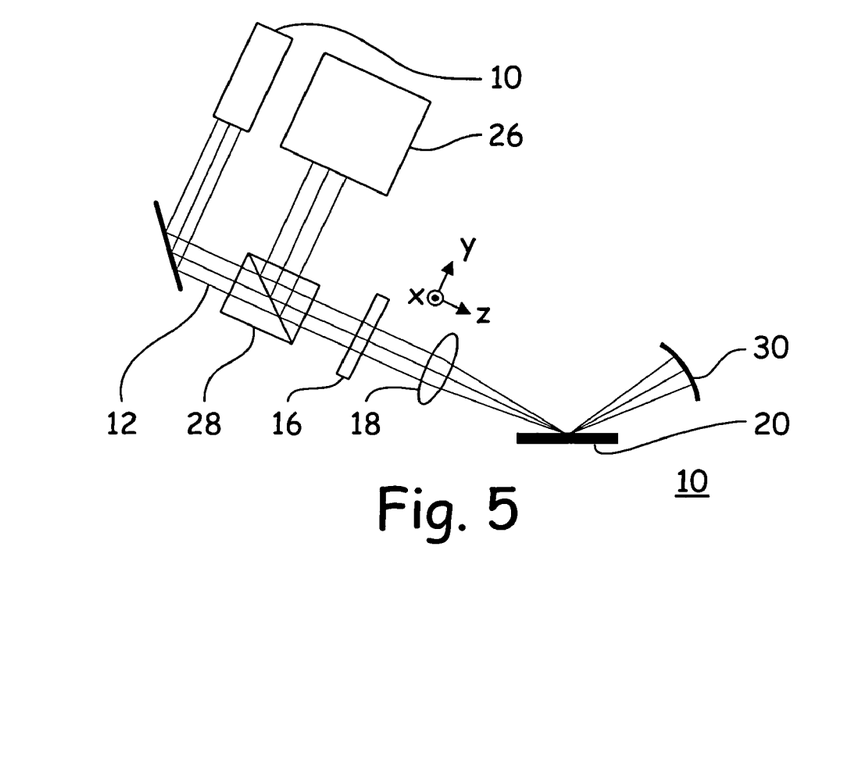
FIG. 5 is a functional diagram of a return path ellipsometer.

The form factor of an ellipsometer 10 according to the preferred embodiments of the present invention is preferably further reduced by using a return-path ellipsometry approach as depicted in FIG. 5. A polarizing beam splitter 28 is preferably used in place of the polarizer 14 and analyzer 24. The collection optics 22 and analyzer 24 are preferably replaced by a concave mirror 30, which sends the beam 12 back through the original path.

The incident angle into the concave mirror 30 preferably does not change the state of polarization, and therefore tends to not introduce any error into the system 10. The light beam 12 reflects off of the substrate 20 twice, which effectively doubles the measurement sensitivity. In addition, the return path configuration is very compact, and thus highly suitable for inline integrated circuit metrology. A further advantage of the design is the effective self-alignment of the replaced polarizer 14 and analyzer 24. The angles of the polarizer 14 and analyzer 24 in ellipsometers are highly correlated, and thus tend to contribute significantly to the system error. With the self aligning replacement of the beam splitter 28, such correlation errors have been effectively eliminated. The ellipsometer depicted in FIG. 5 operates according to the equation:

$$I_{det}=I_0(1+\tan^2 \psi-2 \tan^2 \psi \cos \Delta \cos(2\delta)+(1+\tan \psi)\sin(\Delta)\sin(2\delta))$$

Another aspect of the embodiments of the present invention is to perform focus and tilt on the measurement beam itself. High performance ellipsometry requires very accurate focus and tilt sensors. Normally, a focus and tilt system is attached to the measurement system. However, a focus and tilt sensor that does not use the same beam path as the measurement beam is susceptible to long term drifting and temperature issues. Common probes and focus and tilt beam paths are especially critical for inline integrated circuit metrology, due to the high level of vibration that such systems are subjected to. Typically, the probe beam 12 is not used for such focus and tilt calibrations because it is relatively inaccessibility.

Figure 6:
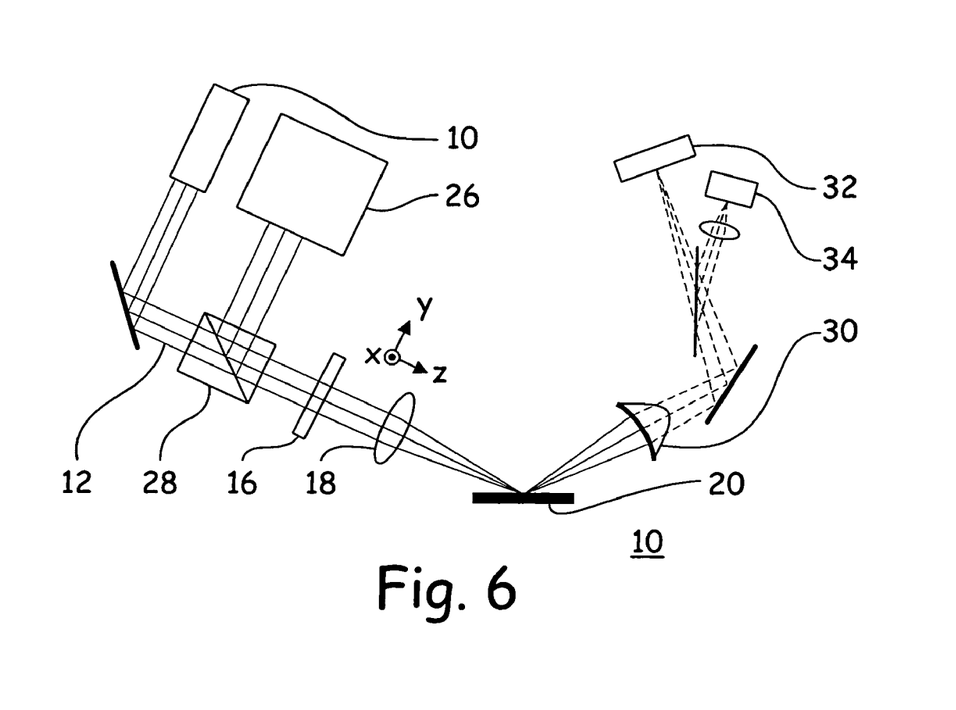
FIG. 6 is a functional diagram of a return path ellipsometer, with focus and tilt detectors that work off the sensing beam.

In an ellipsometer, one simply cannot tag out some of the light anywhere along the probe beam 12, since it tends to change the polarization of the beam 12, which is being measured. Taking light 12 after the analyzer 24 will not affect the measurement itself. However, that is not a good place to put more optics, as it is already a very crowded location within the ellipsometer. However, with the return path configuration as depicted in FIG. 5, the space behind the return mirror 30 is effectively cleared out, and there is room for the focus and tilt sensor. This can be achieved by using a semi-transparent mirror 30 to let some of the light 12 pass through, as depicted in FIG. 6. This approach does not alter the state of polarization on the probe beam 12. Thus, a conventional focus 32 and tilt 34 sensor can be implemented without compromising the accessibility and serviceability of the system 10.

Figure 7:
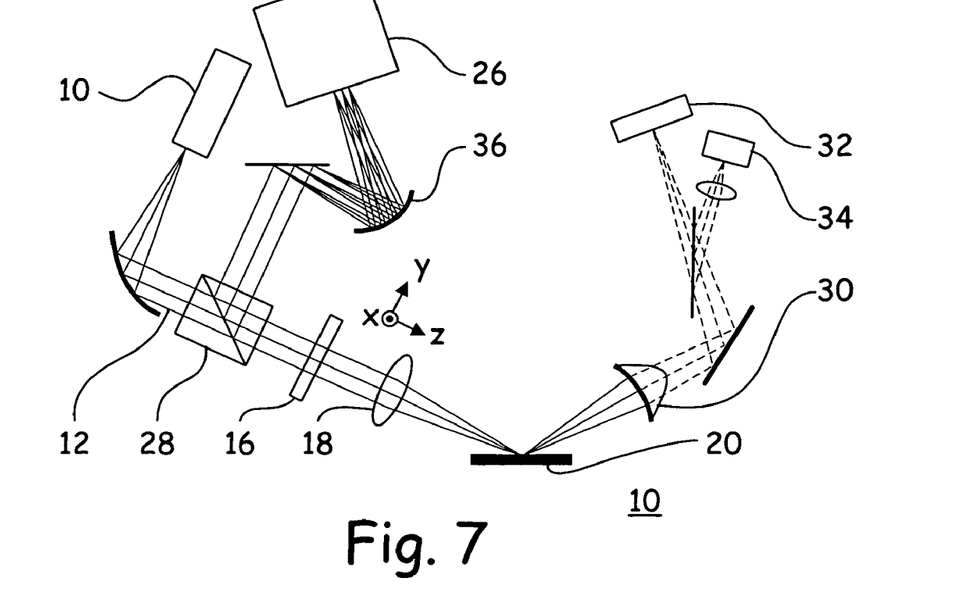
FIG. 7 is a functional diagram of a spectroscopic return path ellipsometer.

Another aspect of the current invention is spectroscopic ellipsometry without moving parts, as depicted in FIG. 7. The advantage of spectroscopic ellipsometry is that it obtains information on the whole spectrum, or at least a greater portion of the spectrum than traditional ellipsometry, including all the lithographic wavelengths of interest, and it more accurately detects the process drift that might affect the spectral content. One of the requirements for spectroscopic ellipsometry is the use of a smaller numerical aperture at the focus and collection optics, as the average larger numerical aperture can wash out the fringe variation that the spectroscopic ellipsometer is trying to detect. The ellipsometer depicted in FIG. 7 operates according to the equation:

$$I_{det}(\lambda)=I_0(1+\tan^2 \psi(\lambda)-2 \tan^2 \psi(\lambda)\cos \Delta(\lambda)\cos(2\delta(\lambda))+(1+\tan \psi(\lambda))\sin(\Delta(\lambda))\sin(2\delta(\lambda)))$$

$$\delta(\lambda,x)=a(\lambda)x=(n_e(\lambda)-n_o(\lambda))\tan(\alpha)x$$

Furthermore, it is desirable to use reflective optics for a broad wavelength range spectroscopic ellipsometer, such as that manufactured by KLA-Tencor Technologies Corporation of Milpitas Calif. A wavelength dispersion grating 36, which may even be a concave cylindrical grating 36 as depicted in FIG. 7, is preferably used before projecting the light 12 into the detector 26. Therefore, the detector 26 output becomes a function of the phase retardation at the wave plate on the compensator 16 (X-axis), and wavelength (Y-axis). The analysis is similar to the single wavelength multi angle case. The ellipsometric parameters at each wavelength can be obtained. Because it detects Δ instead of cos Δ, the present system 10 is more sensitive to very thin films, as compared to a rotating polarizer or rotating analyzer spectroscopic ellipsometer.

It is very useful to obtain ellipsometric parameters in both angle and wavelength. The angular dependent parameters can deduce thickness and other parameters at a specific wavelength. One approach is to perform measurements on one wavelength at a time, using either multiple lasers or lamps with a monochrometer. The draw back of this approach is that the throughput of such a system is not very good. Such measurements are practically limited to only a few wavelengths, because of the time required to make the repeated measurements. Spectroscopic ellipsometry, on the other hand, covers the desired wavelength range, by relying on a dispersion model. The system performance is thus dependant on the goodness of the model that is used. The number of degrees of freedom in these models is preferably as few as possible for good matching and precision. The goodness of fit for the models to the process variation really determines the performance of the system. Therefore, much effort goes into recipe development and multi-sample substrate sets.

Figure 8:
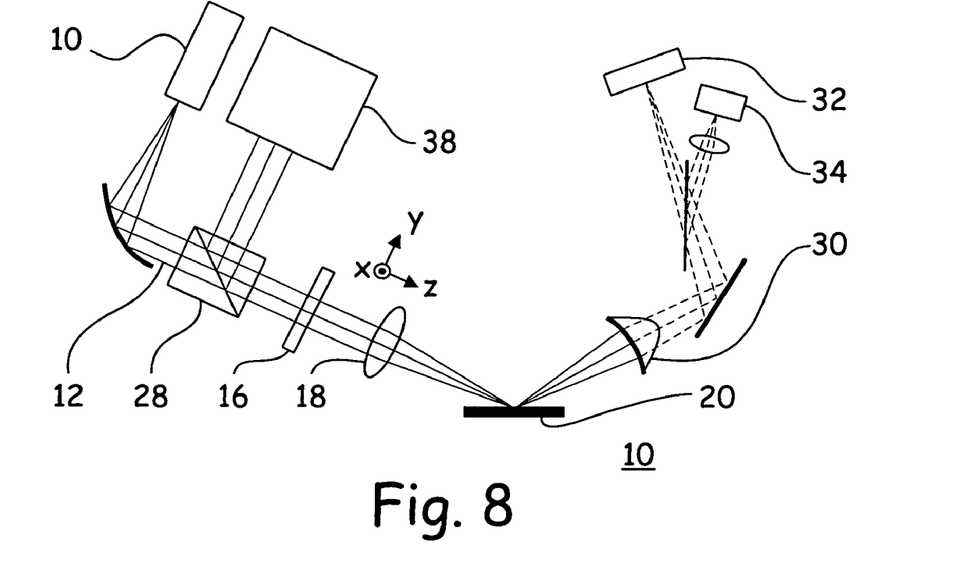
FIG. 8 is a functional diagram of a return path ellipsometer, that measures the ellipsometric parameters in both angle and wavelength with a Fourier transform spectrometer.

Another aspect of the present invention is to measure the ellipsometric parameters in both angle and wavelength as shown in FIG. 8, which uses a Fourier transform spectrometer to form a hypercube image, that contains both spatial and spectral intensity variations. A static Fourier transform hyper spectral image can be used for this purpose. One such Fourier transform hyper spectral imager is described by Wilson and Rafert of Michigan Technological University and Zhan Bin and Zhao, in SPIE vol. 4087, 957 (2000), the disclosure of which is included by reference herein as if laid out in its entirety.

Figure 9:
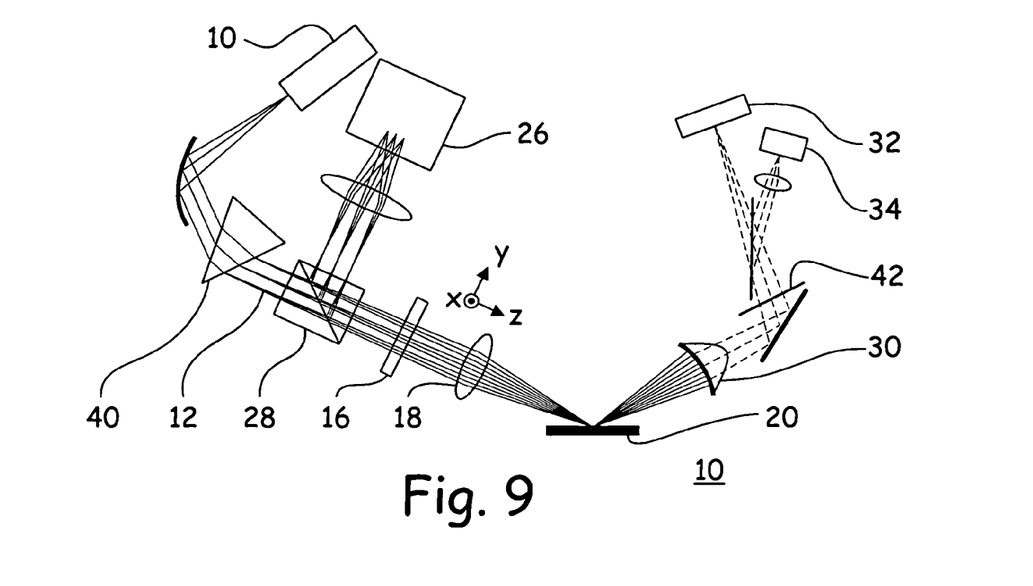
FIG. 9 is a functional diagram of a return path ellipsometer, with spatial spectrum separation to reduce noise.

The spectral information overlays the spatial image with a complex interference pattern. One of the draw backs of this approach is the noise that is added to the image resolution due to the overlay interference pattern. This noise can be reduced by widely separating the spatial spectrum content, such as by using a prism 40 as depicted in FIG. 9, so that they can be easily separated out. The spatial variation is in the ellipsometer according to the present invention preferably varies slowly, according to the design of the Babinet compensator and wave plate combination 16.

Because of the wide wavelength range used in spectroscopic ellipsometry, the interference pattern that it produces also has a large dynamic range. The signal to noise ratio can be reduced by designing and optical filter 42, as depicted in FIG. 9, to control the spectral content in the light 12, so that the spatial content due to the spectrum can be distinguish from the image intensity variation. This type of filter can by tailored to the specific needs of the application, in terms of the wavelength range needed, and throughput and performance requirements.

In general, the most sensitive angle of incidence for ellipsometry is near the Brewster angle for the substrate, which for integrated circuit processing is typically silicon. However, the sensitivity curve generally shifts to angles of incidence that are lower than the Brewster angle for many applications at deep ultra violet and vacuum ultra violet wavelengths. One way to operate at an optimum angle is to build deep ultra violet and ultra violet-visible spectroscopic ellipsometers that have modules with different angles of incidence that are optimized for each wavelength region, such as about 63 degrees and 71.5 degrees for the deep ultra violet and ultra violet visible ranges, respectively.

Figure 10:
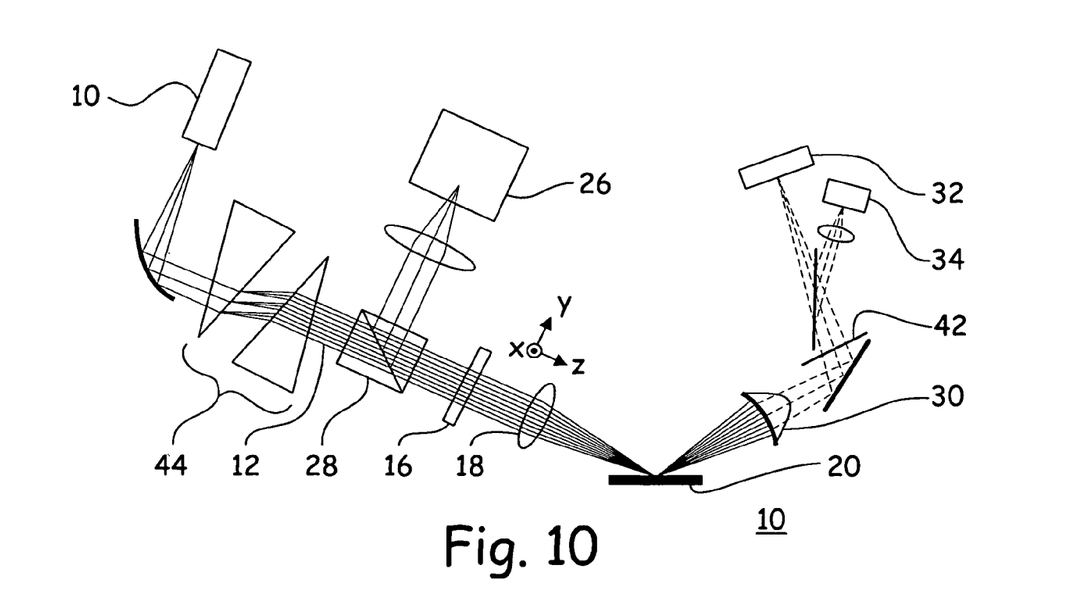
FIG. 10 is a functional diagram of a return path ellipsometer, with a wavelength dependent angle of incidence.

However, there are many other issues with the two module approach, including cost, reliability, form factor, calibration, and subsystem to subsystem matching. It is another aspect of this invention to construct a spectroscopic ellipsometer 10 with a wavelength dependent angle of incidence as depicted in FIG. 10. A dispersive element 44, such as a prism pair, is preferably used to displace the beam 12 according to the wavelength components of the beam 12. The displaced beam 12 is preferably arranged in such a way that the shorter wavelengths strike the top of the focusing mirror/lens with the near infra red wavelengths near the bottom. The light spectrum 12 focuses down to the substrate 20 and is collected in much the same way as discussed above.

The ellipsometric parameters are developed as a function of wavelength and angle of incidence. The angle of incidence correlates with the wavelength, which is relatively larger for near infra red and relatively smaller for deep ultra violet and vacuum ultra violet. The ellipsometer 10 is preferably optimized for sensitivity over the entire desired wavelength range. Because the Babinet compensation creates periodic changes in the intensity of the light 12 along the x axis of each wavelength of the light 12, the fringes can further be used for calibration against drifts in the wavelength.

Thus, the present invention provides a new concept of ellipsometry without moving parts, which uses a compensator with known birefringence along one direction. Preferably, the compensator is a Babinet compensator. The ellipsometer provides for complete determination of the ellipsometric parameters tan $\psi$ and $\Delta$ for each wavelength and angle of incidence.

The ellipsometer disclosed herein has a return path implementation that is space saving, improves sensitivity, and eliminates debilitated optical components and reduces calibration parameters.

The ellipsometer disclosed herein has focus and tilt sensors that use a common beam path as the probe beam, guarding against mechanical drift due to vibration, temperature, and stress.

The ellipsometer disclosed herein has no moving parts, and therefore is faster, less sensitive to lamp noise, more reliable, and has a smaller form factor.

With the ellipsometer disclosed herein, it is possible to vary the angle of incidence, optimizing the sensitivity to the film measurement across the entire supported spectral range.

The ellipsometer disclosed herein uses a Fourier transform imager to obtain ellipsometric parameters as a function of wavelength and angle of incidence.

The ellipsometer disclosed herein improves the signal to noise ratio by optimizing the Babinet compensator and the spectral content of the incidence light.

The ellipsometer disclosed herein enables correction of wavelength drift using the fringes of the light beam, through the use of the Babinet compensator.

The ellipsometer disclosed herein is especially suitable for inline integrated circuit metrology because of the use of a common probe beam diagnostic to compensate for the vibration and mechanical induced drifts.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. In an ellipsometer having a non moving compensator for receiving a probe beam of light along a probe beam path, the improvement comprising:

(a) the compensator adapted to variably retard at least portions of the probe beam along at least one axis of the compensator, thereby changing an orientation of the light passing through the compensator, (b) a polarizing beam splitter, (c) a concave mirror that sends a probe beam back through the probe beam path, and (d) the ellipsometer not having collection optics, a polarizer, and an analyzer.

2. The ellipsometer of claim 1, wherein the compensator is adapted with a fast varying retardation axis and a slow varying retardation axis.

3. The ellipsometer of claim 1, wherein the compensator is adapted with a fast varying retardation axis aligned substantially along an x axis of the compensator, and a slow varying retardation axis aligned substantially along a y axis of the compensator.

4. The ellipsometer of claim 1, wherein the compensator is a Babinet compensator.

5. The ellipsometer of claim 1, wherein the compensator is adapted with a wave plate disposed on a surface of the compensator, the wave plate having sub wavelength-spaced grooves, disposed in pixel groups, that are aligned along different orientations.

6. The ellipsometer of claim 1, wherein all elements of the ellipsometer that are disposed along the probe beam path do not move during ellipsometric measurement operations.

7. The ellipsometer of claim 1, wherein all elements of the ellipsometer that are disposed along the probe beam path are fixed.

8. The ellipsometer of claim 1, wherein the concave mirror is partially reflective, and at least one of a focus sensor, a tilt sensor, and combination focus and tilt sensor are disposed behind the concave mirror, which enables calibration of the ellipsometer on the probe beam.

9. The ellipsometer of claim 1, wherein the ellipsometer is a spectroscopic ellipsometer having a cylindrical mirror for separating wavelengths of the probe beam as it enters a detector.

10. The ellipsometer of claim 1, wherein the ellipsometer measures ellipsometric parameters in both angle and wavelength with a Fourier transform spectrometer.

11. The ellipsometer of claim 1, wherein image resolution noise is reduced by separating a spatial spectrum content of the probe beam with at least one of a prism and grating.

12. In an ellipsometer having a fixed, non rotating compensator for receiving a probe beam of light along a probe beam path, the improvement comprising:
the compensator adapted to variably retard at least portions of the probe beam along at least one axis of the compensator, thereby changing an orientation of the light passing through the compensator,
a concave mirror that sends the probe beam back through the probe beam path,
the ellipsometer not having collection optics, a polarizer, and an analyzer; and
a dispersive element that displaces the probe beam according to wavelength components of the probe beam, with shorter wavelengths of the probe beam striking a top of a focusing element, and longer wavelengths of the probe beam striking a bottom of the focusing element, thereby providing the ellipsometer with a wavelength dependent angle of incidence.

13. In an ellipsometer having a non moving compensator for receiving a probe beam of light along a probe beam path, the improvement comprising:
the compensator adapted to variably retard at least portions of the probe beam along at least one axis of the compensator, thereby changing an orientation of the light passing through the compensator, and
a polarizing beam splitter, and a concave mirror which sends the probe beam back through the probe beam path, the ellipsometer not having collection optics, a polarizer, and an analyzer.

14. The ellipsometer of claim 13, wherein the elements of the ellipsometer that are disposed along the probe beam path are fixed and do not rotate.

15. The ellipsometer of claim 13, wherein the ellipsometer is a spectroscopic ellipsometer having a cylindrical mirror for separating wavelengths of the probe beam as it enters a detector.

16. The ellipsometer of claim 13, wherein the ellipsometer measures ellipsometric parameters in both angle and wavelength with a Fourier transform spectrometer.

17. In an ellipsometer having a fixed, non rotating compensator for receiving a probe beam of light along a probe beam path, the improvement comprising:
the compensator adapted to variably retard at least portions of the probe beam along at least one axis of the compensator, thereby changing an orientation of the light passing through the compensator, and
a polarizing beam splitter, and a concave mirror which sends the probe beam back through the probe beam path, the ellipsometer not having collection optics, a polarizer, and an analyzer, where the concave mirror is partially reflective, and at least one of a focus sensor, a tilt sensor, and combination focus and tilt sensor are disposed behind the concave mirror, which enables calibration of the ellipsometer on the probe beam.

18. An ellipsometer comprising:
a light source for generating a probe beam of light along a probe beam path,
a polarizing beam splitter for passing the probe beam along the probe beam path, at least in part, as the probe beam passes through the beam splitter in a first direction, and for diverting the probe beam along a detection path, at least in part, as the probe beam passes through the beam splitter in a second direction that is substantially opposite of the first direction,
a compensator adapted to variably retard at least portions of the probe beam along at least one axis of the compensator, thereby changing an orientation of the light passing through the compensator,
optics for focusing the probe beam on a spot on a substrate,
a concave mirror that receives the probe beam from the spot on the substrate as it travels along the probe beam path in the first direction, and sends the probe beam back along the probe beam path in the second direction, and
a detector for receiving the probe beam along the detection path,
wherein the beam splitter, compensator, optics, mirror, and detector are non moving relative to the probe beam.

* * * * *